United States Patent

Holcombe et al.

[11] Patent Number: 5,368,029
[45] Date of Patent: Nov. 29, 1994

[54] INTEGRAL CATHETER AND BLOOD TESTER

[76] Inventors: David A. Holcombe, 6 Colorido, Rancho Santa Magarita, Calif. 92688; Brent W. Poole, 861 Hedges Dr., Corona, Calif. 91720

[21] Appl. No.: 869,452

[22] Filed: Apr. 16, 1992

[51] Int. Cl.⁵ .................................................. A61B 5/00
[52] U.S. Cl. ........................................ 128/636; 128/637; 128/917
[58] Field of Search ............... 128/632, 636, 637, 917; 604/169, 192

[56] References Cited

U.S. PATENT DOCUMENTS

| | | | |
|---|---|---|---|
| 4,553,552 | 11/1985 | Valdespino et al. | 128/637 |
| 4,959,196 | 9/1990 | Moisson | 128/632 |
| 5,029,583 | 7/1991 | Meserol et al. | 128/637 |

Primary Examiner—Lee S. Cohen
Assistant Examiner—Marianne Parker
Attorney, Agent, or Firm—Roy A. Ekstrand

[57] ABSTRACT

An integral catheter and blood tester includes a needle unit which is receivable within a conventional catheter intravenous tube and housing. The catheter supports a piercing needle and interior chamber. A transparent tester housing is coupled to the needle unit and supports a test strip and test patch which extends into the flash chamber of the catheter needle. A constricting valve surrounds the test strip to maintain closure of the flash chamber. Once the catheter and needle have been inserted into the desired blood vessel, a quantity of blood is introduced into the flash chamber so as to wet the test patch. The test patch may, for example, include conventional litmus material used to test the pH of the test sample. Once the flash process is complete, the needle and tester housing are withdrawn from the catheter to permit conventional intravenous coupling to the catheter. Thereafter, the tester housing is separable from the needle unit to permit discarding of the needle unit. The separation process causes the test strip to be wiped substantially clean of excess blood by the constricting valve. The tester housing provides a protective clear shield about the contaminated test patch which facilitates visual examination thereof while precluding inadvertent contact with the blood contaminated test patch.

17 Claims, 4 Drawing Sheets

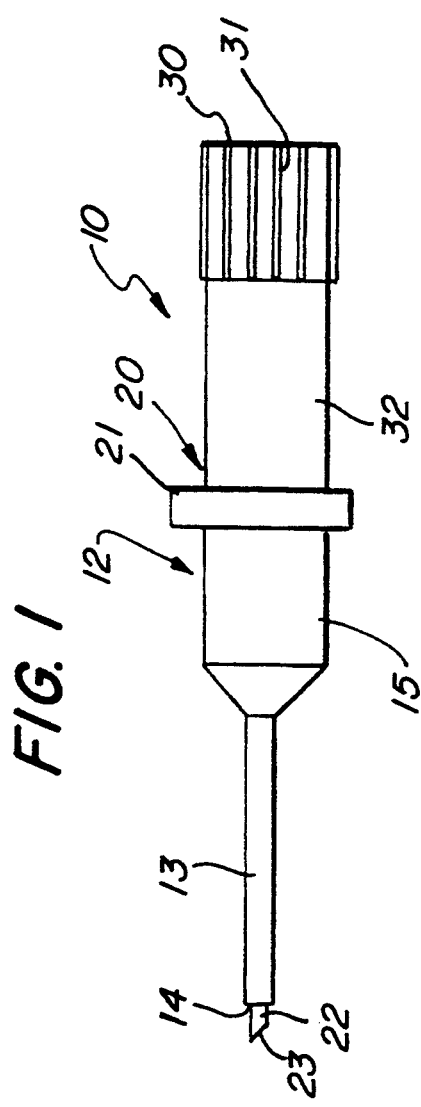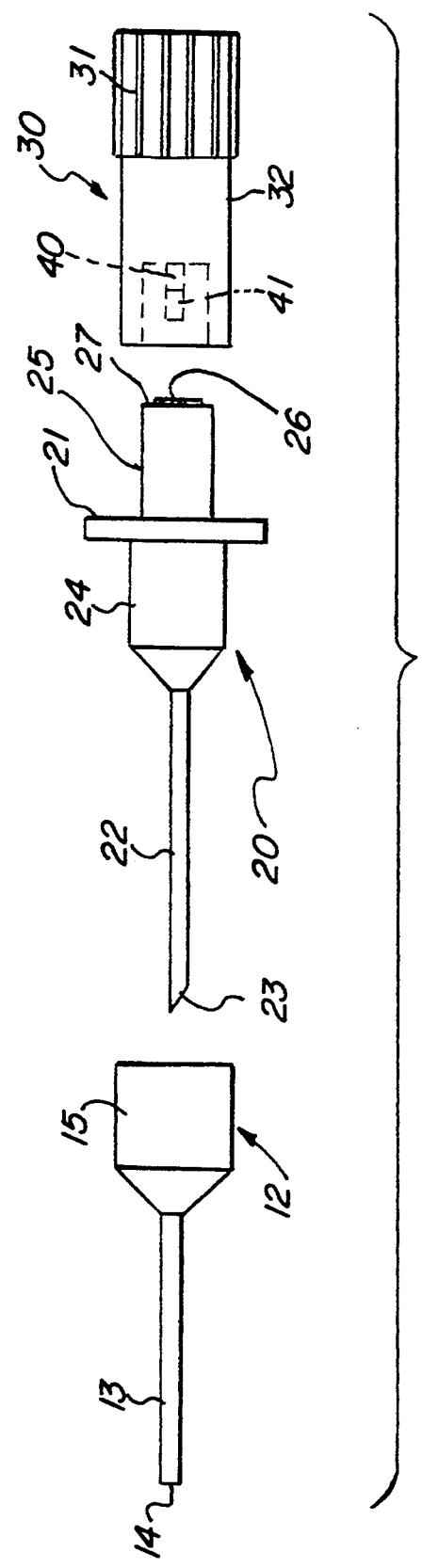

INTEGRAL CATHETER AND BLOOD TESTER

FIELD OF THE INVENTION

This invention relates generally to blood testing systems and particularly to those used in a combination with a catheter or the like.

Background of the Invention

Medical practitioners have, throughout history, faced a variety of risks associated with the practice of their professions. The danger of contamination or infection from substances handled and people treated has virtually always threatened medical practitioners. Despite this, practitioners have, for the most part, willingly assumed this risk while observing certain precautions and preventative measures. However, the recent dramatic increase in the nature and types of risks to which medical practitioners are exposed has, in many instances, rendered standard precautionary measures insufficient to protect the practitioner. Of particular danger is the dramatic increase in blood and fluid born infectious diseases such as AIDS or the like. The potential infection for medical practitioners in contact with blood and other body fluids of their patients has required the use of sometimes elaborate and cumbersome protective measures.

One source of great risk arises from the variety of needles and cutting instruments used by medical practitioners. The great number of hypodermic needles, syringes and catheters used places the medical practitioner in virtually constant danger of being infected by an inadvertent piercing of the practitioner's skin with a contaminated needle.

Of the many types of medical needles used by medical practitioners, those known generally as catheters may pose a significantly greater danger of infection or contamination to the practitioner due to the increased handling required in their use. The most common catheters utilize an elongated hollow intravenous tube having a small housing which receives an elongated pointed catheter needle which extends beyond the tube end. A housing coupled to the opposite end of the needle defines a small chamber and a suitable coupling mechanism which may be used to provide connection to a intravenous feeding tube or the like.

In its normal use, the catheter unit having the catheter needle received therein is used to pierce the skin and the wall of the target blood vessel to a sufficient depth that the intravenous tube end is carried into the target blood vessel. Thereafter, finger pressure is applied to preclude blood flow as the piercing needle is withdrawn. A small amount of blood is allowed to flow outwardly through the catheter tube into the housing in a process known as "flashing" prior to the removal of the needle to assure that the catheter has been properly placed within the target vessel. Thereafter, finger pressure is again applied and the needle is completely withdrawn afterwhich connection is made between the catheter unit housing and the supply of intravenous material solution which is sought to be introduced into the patient's bloodstream.

In many situations, such as emergency treatment by paramedics or other emergency response practitioners, additional operations are carried forward to obtain blood sample testing at the emergency scene or in route to the hospital as advance information is forwarded to the response team waiting at the hospital. Such tests may include, for example, vital information such as blood sugar or blood pH and so on. These tests are conducted by obtaining a blood sample during the flashing operation which is smeared upon a test strip and then after a predetermined waiting period wiped from the test strip and visually compared to standard criteria such as color charts and so on.

The problems of providing such intricate and careful handling of blood contaminated articles in the confusing, noisy and excited environment of the trauma site or the ambulance ride back to the hospital greatly increase the chance of infection or contamination of the medical practitioner.

Various systems have been provided by practitioners in the art for measuring elements of blood chemistry as well as preventing infection of medical practitioners handling needles.

For example, U.S. Pat. No. 4,883,461 issued to Sawyer sets forth a SAFETY NEEDLE SHEATH IN ANTI-REFLUX CATHETER HAVING NOVEL VALVE MEANS in which a catheter includes a tubular structure together with a anti-reflux valve which responds to the blood reflux to close while opening in response to positive fluid pressure within the tubular structure.

U.S. Pat. No. 4,643,192 issued to Fiddian-Green sets forth HOLLOW VISCUS TONOMETRY. The apparatus relies upon the fact that ischemia in a hollow internal organ can be detected in its incipient stages by obtaining a carbon dioxide sample from within the organ of interest and measuring the carbon dioxide partial pressure therein. This measurement together with measurement of bicarbonate concentration and the pH of the organ wall provide an indication of the onset of ischemia. The apparatus used includes an elongated probe received within the blood vessel of concern.

U.S. Pat. No. 4,703,756 issued to Gough, et al. sets forth a COMPLETE GLUCOSE MONITORING SYSTEM WITH AN IMPLANTABLE TELEMETERED SENSOR MODULE in which a module having two oxygen sensors is situated in an oxygen permeable housing in a tandem relationship. The module includes a communication capability for transmitting measurement information to an external recording device outside the body.

U.S. Pat. No. Re.31,879 issued to Lubbers, et al. sets forth a METHOD AND ARRANGEMENT FOR MEASURE THE CONCENTRATION OF GASES in which a monochromatic light beam is generated having a predetermined color characteristic. An indicator generates light signals indicative of the concentration of gases in a sample to be measured which includes a light transmissive surface positioned to be impinged by the monochromatic light beam.

U.S. Pat. No. 4,871,351 issued to Feingold sets forth an IMPLANTABLE MEDICAL INFUSION SYSTEM including an implantable unit, a refillable reservoir, a catheter connected thereto and a pumping mechanism activated by a microcomputer for pumping medication from the reservoir through the catheter into the body.

While the foregoing described prior art devices have provided some assistance to medical practitioners and while other devices have been devised directed primarily at preventing the inadvertent piercing of the skin surface of a medical practitioner handling contaminated needles, little if any attention has been provided by practitioners in the medical arts to the problem of making the handling of blood sampling under emergency conditions safer for medical practitioners.

Summary of the Invention

Accordingly, it is a general object of the present invention to provide an improved blood tester. It is a more particular object of the present invention to provide an improved and safer blood tester for use under emergency circumstances.

In accordance with the present invention, there is provided for use in testing a blood sample during the insertion of a catheter within a blood vessel, an integral catheter and blood tester comprises: a catheter having a hollow tube; a needle unit having a needle unit housing partially receivable within the catheter defining an interior chamber and having a needle extending from the chamber terminating in a piercing end; a blood tester having a blood tester housing couplable to the needle unit and a test strip supporting a test patch, the test patch extending into the interior chamber when the blood tester housing is coupled to the needle unit; valve means supported by the needle unit for receiving the test strip and test patch and for wiping blood from the surfaces thereof when the blood tester housing and the needle unit are separated; and shield means supported by the blood tester housing partially surrounding the test strip and test patch.

BRIEF DESCRIPTION OF THE DRAWINGS

The features of the present invention, which are believed to be novel, are set forth with particularity in the appended claims. The invention, together with further objects and advantages thereof, may best be understood by reference to the following description taken in conjunction with the accompanying drawings, in the several figures of which like reference numerals identify like elements and in which:

FIG. 1 sets forth a side view of an integral catheter and blood tester constructed in accordance with the present invention;

FIG. 2 sets forth an assembly view of an integral catheter and blood tester constructed in accordance with the present invention;

DESCRIPTION OF THE PREFERRED EMBODIMENTS

Figure 3A:
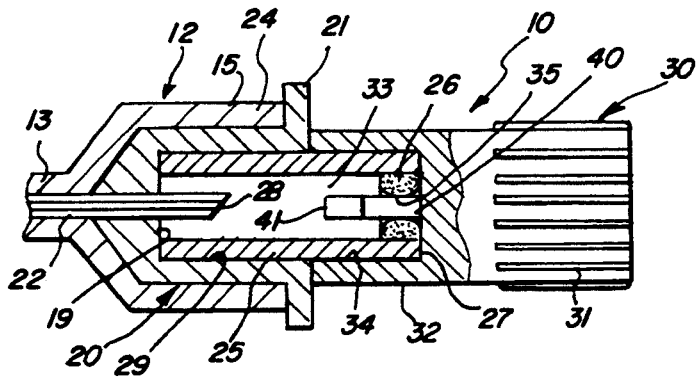
FIG. 3A and 3B set forth partially sectioned side views of the present invention embodiment of FIG. 1 in connected and disconnected relationship respectively.

FIG. 1 sets forth a side view of an integral catheter and blood tester constructed in accordance with the present invention and generally referenced by numeral 10. Catheter and blood tester 10 includes a catheter unit 12 having a generally cylindrical housing 15 coupled to an elongated cylindrical hollow intravenous tube 13. Intravenous tube 13 defines an end portion 14. A needle unit 20 includes an outwardly extending flange 21, a cylindrical housing 24 (seen in FIG. 2) and an elongated cylindrical catheter needle 22. Catheter needle 11 extends beyond end 14 of intravenous tube 13 in the assembled position shown in FIG. 1 and defines a pointed end 23. A tester housing 30 defines a generally cylindrical viewing portion 32 coupled to needle unit 20 and a cylindrical grip end 31. FIG. 1 shows the assembled position of catheter and blood tester 10 appropriate to the insertion of catheter and blood tester into the target blood vessel of a patient. During this insertion, the extended pointed end 23 of catheter needle 22 provides the implement for piercing the patient's skin and underlying tissue as well as the blood vessel wall forming a pierced hole therein through which end portion 14 of intravenous tube 13 may be passed. In its typical use, catheter and blood tester 10 are inserted in the assembled position shown until end portion 14 and pointed end 23 are reliably positioned within the target blood vessel.

FIG. 2 sets forth an assembly view of catheter and blood tester 10. As described above, catheter 12 includes a generally cylindrical housing 15 and an extended generally cylindrical hollow intravenous tube 13. The latter terminates in an end portion 14. Needle unit 20 defines a generally cylindrical housing 24 having an outwardly extending flange 21. Needle unit 24 further includes an elongated generally cylindrical catheter needle 22 extending from housing 24 and terminating in a pointed end 23. Needle unit 20 further includes a generally cylindrical sleeve 25 extending from housing 24 and terminating in an end portion 27. A valve 26 is supported at end 27 of sleeve 25 and is shown below in greater detail. A tester housing 30 defines a generally cylindrical viewing portion 32 and an end grip portion 31. Tester housing 30 supports a test strip 40 within viewing portion 32 which in turn supports a test patch 41.

In operation, tester housing 30 is received upon sleeve 25 in the manner set forth below in greater detail to couple tester housing 30 to needle unit 10 in the manner shown in FIG. 1. The combined structure of tester housing 30 and needle unit 20 are received within catheter 12 such that catheter needle 22 extends through intravenous tube 13 and beyond to expose point end 23 of catheter needle 22 in the manner shown in FIG. 1. Thereafter, catheter and blood tester 10 may be used in the above-described manner to pierce the patient's skin, underlying tissue and the wall of the target blood vessel. Once the piercing has been completed, a quantity of the patient's blood is permitted to flow through catheter needle 22, housing 24 and into sleeve 25. By means set forth below in greater detail, test strip 40 and valve 26 cooperate to preclude the further flow of blood beyond sleeve 25 at valve 26. Once the desired quantity of blood has been introduced into housing 24 and sleeve 25 of needle unit 20, further blood flow is precluded by common measures such as appropriate finger pressure upon the blood vessel. In accordance with an important aspect of the present invention, test patch 41 is exposed to the blood flash within sleeve 25 during the above-described flashing operation. Once it has been determined that the intravenous tube and catheter needle have been properly placed within the target blood vessel, needle unit 20 and tester 30 may be withdrawn as a single unit from catheter 12. Thereafter, needle unit 20 and tester housing 30 may be separated and needle unit 20 discarded in accordance with appropriate safety techniques of needle handling. The appropriate coupling to catheter 12 may be then completed permitting the desired intravenous fluid introduction to take place.

In accordance with an important aspect of the present invention described below in greater detail, valve 26 and test strip 40 cooperate to remove excess blood from test strip 40 and test patch 41 as needle unit 20 and tester housing 30 are separated. As a result, tester housing 30 maintains test strip 40 and test patch 41 within the enclosure of housing 30. Because test patch 41 has been exposed to the blood flash within needle unit 20, it may be utilized in the above-described blood testing such as measuring the pH of the patient's blood. In its preferred form, tester housing 30 is fabricated of a transparent material such as molded plastic or the like and thus test patch 41 may be readily observed within the interior of tester housing 30 without exposing the practitioner to contact with the blood contaminated test strip or test patch. Thus, the practitioner is able to clearly view test patch 41 through the transparent material of viewing portion 32 while holding tester housing 30 at a convenient point upon grip end portion 31.

It will be apparent to those skilled in the art that the convenient manner in which catheter and blood tester 10 is utilized and the avoidance of any handling by the medical practitioner of a blood contaminated element during the blood testing process provides substantial safety for the medical practitioner while facilitating the desired blood testing. It will be equally apparent to those skilled in the art that while test patch 41 is described as having a pH testing material such as litmus or the like, other test media may be utilized to perform other blood tests without departing from the spirit and scope of the present invention.

FIG. 3A sets forth a section view of catheter and blood tester 10 in the assembled or connected configuration corresponding to FIG. 1. A needle unit 20 defines a generally cylindrical housing 15 having an outwardly extending flange 21. Housing 15 further defines an internal generally cylindrical cavity 29 having a closed end 19. Housing 15 further supports an extending elongated catheter needle 22. As is set forth in FIG. 1, catheter needle 22 terminates in a pointed end 23 at the outer end thereof. The remaining end of catheter needle 22 extends through closed end 19 of housing 15 and terminates within cavity 29 in an open end 28. An elongated generally cylindrical sleeve 25 defines an interior flash chamber 33 and is sealingly received within and secured to the interior surface of cavity 29 of housing 15. A portion of sleeve 25 extends outwardly from cavity 19 beyond flange 21 and terminates in an end portion 27. End portion 27 supports a valve 26 having a sealing orifice 35 formed at the center portion thereof.

A tester housing 31 preferably formed of a clear transparent molded plastic material or the like defines a generally cylindrical viewing portion 32 and a grip end 31. Tester housing 30 further defines a cylindrical interior cavity 34 having a closed end 27. An elongated test strip 40 is supported within cavity 34 of tester housing 30 and extends into cavity 34 from the interior end of cavity 34. Test strip 50 supports a test patch 41 on the end portion thereof. In its preferred form, test strip 40 and test patch 41 are formed having a generally cylindrical cross section which cooperates with sealing orifice 35 of valve 26 to permit test strip 40 to be inserted through orifice 35 and into flash chamber 33 in a sealing engagement when tester housing 40 is coupled to needle unit 20 by the insertion of end 27 of sleeve 25 into cavity 34. Thus, in the assembled position shown in FIG. 3A, tester housing 40 is received upon sleeve 2 and secured thereto by a frictional fit between cavity 34 and sleeve 25. The cooperation of valve 26 and test strip 40 provide a sealing closure of flash chamber 33 and prevent leakage from flash chamber 33 so long as tester housing 30 is secured to needle unit 20. In accordance with an important aspect of the present invention, test strip 40 supports test patch 41 within flash chamber 33 to expose test patch 41 to the blood flow into chamber 33 during the above-described flashing process.

Catheter 12 includes an intravenous tube 13 and cylindrical housing 15. Housing 15 receives catheter housing 24 while intravenous tube 13 receives catheter needle 22 in the above-described assembly.

In operation, the above-described insertion process is carried forward placing catheter needle 22 and intravenous tube 13 in communication with the target blood vessel. Thereafter, the above-described blood flashing process permits a quantity of the patient's blood to flow outwardly through catheter needle 22 from end 28 thereof into the interior of flash chamber 33. This blood fills flash chamber 33 and immerses test patch 41 within the patient's blood. Thereafter, once the medical practitioner has observed the blood flashing within chamber 33 and thereby confirmed the proper placement of catheter needle 22 and intravenous tube 13, the combined structures of needle unit 20 and tester housing 30 may be removed from catheter 12 in the above-described procedure.

Figure 3B:
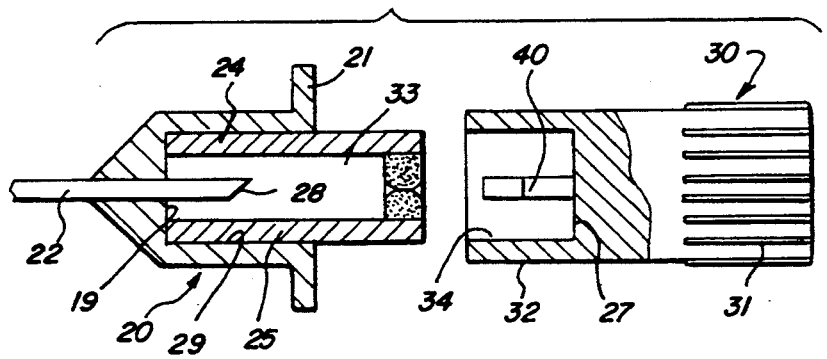

FIG. 3B sets forth catheter and blood tester 10 following the removal of needle unit 20 and tester housing 30 from catheter 12 and the separation of tester housing 30 from needle unit 20. As described above, needle unit 20 is discarded in accordance with appropriate safety precautions and techniques. In accordance with an important aspect of the present invention, tester housing 30 is separated from needle unit 20 by drawing housing 30 axially and thereby withdrawing the extending portion of sleeve 25 from cavity 34. The separation of tester housing 30 from needle unit 20 also withdraws test strip 40 and test patch 41 outwardly through orifice 35 of valve 26. Because valve 26 provides a sealing engagement between orifice 35 and test strip 40 as well as test patch 41, the withdrawal of test strip 40 and test patch 41 outwardly through orifice 35 provides a wiping action upon test strip 40 and test patch 41 which removes substantially all of the excess blood therefrom. Once test strip 40 and test patch 41 have been removed through orifice 35, valve 26 closes orifice 35 which restores the seal of flash chamber 33 and captivates the blood within flash chamber 33 to avoid any contact therewith by the medical practitioner.

Once tester housing 30 has been fully separated from needle unit 20, the condition of test patch 41 may be observed through the transparent wall of viewing portion 32. It should be noted that in accordance with an important aspect of the present invention, test patch 41 remains enclosed within the interior of cavity 34 of tester housing 30. Thus, the surrounding surface of viewing portion 32 of tester housing 30 provides a protective covering for the blood contaminated surfaces of test patch 41 and test strip 40. As a result, tester housing 30 may be easily and conveniently handled by the medical practitioner without undue risk of contact with the contaminated test patch. Once the examination of test patch 41 is completed, tester housing 30 may be discarded in accordance with appropriate precautionary techniques.

It will be apparent to those skilled in the art that the present invention integral catheter and blood tester provides a convenient easy to use catheter structure which permits blood testing such as pH measurement or the like by exposing a test patch to the flashed blood sample during catheter insertion while facilitating the safe handling of the exposed test patch using transparent tester housing 30 as a protective housing and shield for the contaminated test patch.

Figure 4A:
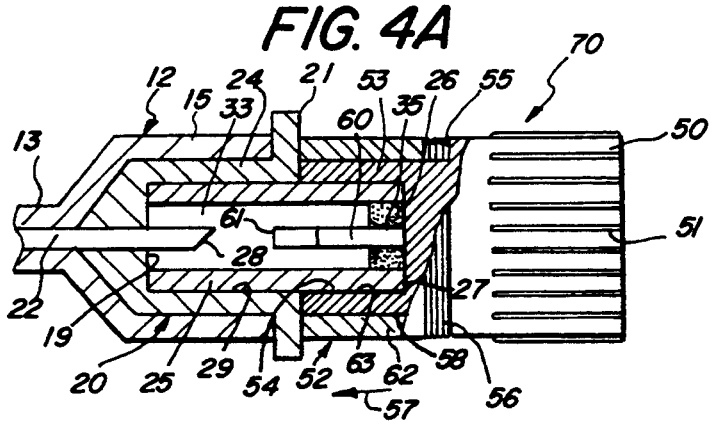
FIGS. 4A and 4B set forth partial sectioned views of an alternate embodiment of the present invention integral catheter and blood tester in connected and disconnected relationships respectively.

FIG. 4A sets forth a partial section view of an alternate embodiment of the present invention catheter and blood tester generally referenced by numeral 70. Catheter and blood tester 70 utilizes catheter 12 and needle unit 20 together with sleeve 25 in the same configuration as shown in the embodiment of FIGS. 1 through 3B. The difference between catheter and tester 70 shown in FIGS. 4A and 4B with the above-described catheter and blood tester referenced by numeral 10 is found in the structure of tester housing 50 which provides an alternate structure for producing additional shielding and protection of the contaminated test strip and which permits the utilization of an extended length test strip 60 and an extended test patch 61.

Specifically, catheter 12 includes a cylindrical housing 15 and an extending intravenous tube 13. Needle unit 20 includes a generally cylindrical housing 24 having an outwardly extending flange 21 and supporting an extending pointed catheter needle 22 having an interior end 28. Housing 24 defines an interior cavity 29 which receives and supports a generally cylindrical sleeve 25. Sleeve 25 is tightly received within cavity 29 in a sealing attachment and secured thereto by conventional methods such as thermal welding, adhesives or the like. In the alternative, housing 24 and sleeve 25 may be fabricated of a single molded plastic part with the essential requirement being the cylindrical extension of end 27 of sleeve 25. Housing 24 further defines a closed end 19 while sleeve 25 defines an interior flash chamber 33. A resilient valve 26 defines a constricting orifice 35 which, under the resilience of valve 26, tends to expand in a inwardly directed radial manner to converge and seal orifice 35 and provide closure of flash chamber 33.

Tester housing 50 defines a generally cylindrical member having a cylindrical grip end 51 and a cylindrical reduced diameter portion 53. Reduced diameter portion 53 defines an outer diameter 58 and an interior cavity 54. In its preferred form, tester housing 50 is formed of a transparent material such as clear molded plastic and thus forms a viewing portion 52 through which the interior of flash chamber 33 may be viewed. Cavity 54 receives end 27 of sleeve 25 during the assembly of tester 50 to needle unit 20 in the manner described above. This fit is preferably a reasonably secure slide fit which tends to maintain the attachment between housing 50 and needle unit 20 but which may be readily overcome when the practitioner desires to separate tester housing 50 from needle unit 20 in the manner described above for the preceding embodiment. Tester housing 50 further includes an inwardly extending test strip 60 supporting a test patch 61 at the end portion thereof. Test patch 61 is formed of a suitable visual indicator type material such as litmus or the like which exhibits a visual change in response to the to-be-examined blood criteria in accordance with conventional blood testing techniques such as pH testing or the like. During the assembly of tester housing 50 to needle unit 20, test strip 60 and test patch 61 are forced through orifice 35 of valve 26. The resilience of valve 26 causes a sealing constriction of orifice 35 about test strip 60 which maintains the sealing closure of flash chamber 33.

Tester housing 50 further supports a generally cylindrical sliding sleeve 62 having an inner diameter 63 which is sufficiently large to permit sliding sleeve 62 to be freely movable upon outer diameter 58 of reduced diameter portion 53. Sliding sleeve 62 is preferably formed of a transparent material such as clear transparent molded plastic or the like. Tester housing 50 further defines a shoulder portion 55 forming an annular shoulder transition between reduced diameter 53 and the larger diameter of grip end 51. A coil spring 56 is captivated between shoulder 55 and the end portion of sliding sleeve 62. In the assembled position shown in FIG. 4A, spring 56 is compressed between shoulder 55 and the end of sleeve 62 and thus provides a spring force urging sleeve 62 in the direction indicated by arrow 57. In the assembled position, however, the frictional attachment of tester housing 50 to sleeve 25 is sufficient to withstand this spring force and thus spring 56 and sleeve 62 remain captivated in the positions shown in FIG. 4A.

In operation, the practitioner carries forward the above-described process of catheter insertion and blood vessel piercing as well as the above-described process of flashing in which a small quantity of blood is permitted to flow through needle 22 partially filling flash chamber 33. Once the visual indication and confirmation of proper catheter placement has been provided by the flashing process, the quantity of blood within flash chamber 33 is in contact with test patch 61 of test strip 60. Test patch 61 undergoes the visual change described above as the to-be-tested chemicals within the blood sample begin reacting upon test patch 61.

Thereafter, the practitioner is able to remove the assembled combination of tester housing 50 and catheter needle unit 20 by withdrawing the assembly outwardly from catheter 12 leaving intravenous tube 13 in place in accordance with conventional practices. Once needle unit 20 and tester housing 50 are removed, the practitioner may then attach suitable intravenous fluid devices to catheter 12 in accordance with conventional methods.

Figure 4B:
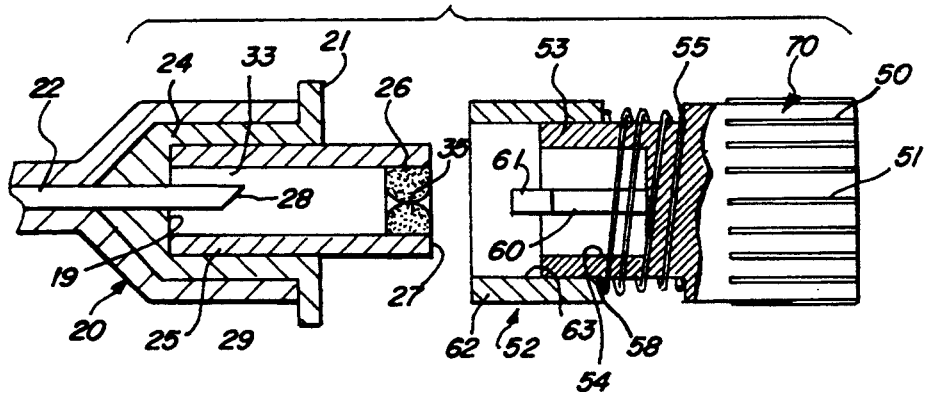

FIG. 4B sets forth the configuration of catheter and tester 70 once needle unit 22 is separated from tester housing 50 in order to discard needle unit 20. This separation is carried forward by producing a drawing force between flange 21 of needle unit 20 and grip end 51 of tester housing 50 which separates sleeve 25 from cavity 54. During the separation of tester housing 50 from needle unit 20, the axial motion as tester housing 50 is drawn outwardly along sleeve 25 simultaneously draws test strip 60 and test patch 61 outwardly through orifice 35 of valve 26. It should be noted that the resilient constriction of orifice 35 provided by valve 26 serves to provide a wiping action upon test strip 60 and test patch 61 which removes excess blood therefrom and permits the ready viewing of test patch 61 substantially free of excess blood which would otherwise obscure the viewing of the test patch. In its preferred form, test strip 60 and test patch 61 are formed in a generally cylindrical shape corresponding to the circular constriction provided by orifice 35 of valve 26. However, it will be apparent to those skilled in the art that other combinations of valve 26, orifice 35 and shapes of test strip 60 and test patch 61 may be utilized without departing from the spirit and scope of the present invention. The essential character of valve 26, orifice 35, test strip 60 and test patch 61 is to provide the wiping action upon test patch 61 and test strip 60 as they are withdrawn through orifice 35.

In addition, as tester housing is removed from needle unit 20, the captivation of spring 56 is released permitting the spring force of spring 56 to urge sleeve 62 in the direction indicated by arrow 57. As seen in FIG. 4B, the repositioning of sleeve 62 provides an extended shield which surrounds test patch 61 of test strip 60 and thus provides additional protection which precludes inadvertent touching of the blood contaminated portions of test patch 60 and test strip 61. As mentioned above, sleeve 62 as well as reduced diameter portion 53 are formed of a transparent clear material such as transparent molded plastic. Thus, the visual condition of test patch 60 having been exposed to the flashed blood sample in the above procedure may be easily observed through the clear material of sleeve 62 and reduce diameter portion 53. The extent of movement of sliding sleeve 62 may be limited in accordance with conventional fabrication techniques such as providing cooperating tabs or the like. However, in the present embodiment, it has been found desirable to secure one end of spring 56 to the interior end of sleeve 62 and thereby limits its motion to the full extension of spring 56. Once the desired examination of test patch 61 has been carried forward, the practitioner may simply discard tester housing 50 in accordance with established procedures. It should be noted that during the entire handling procedure of catheter and blood tester 70, the practitioner has not been required to touch or otherwise contact contaminated blood while performing the above-described testing procedure. This, of course, provides enhanced safety for the medical practitioner.

Figure 5A:
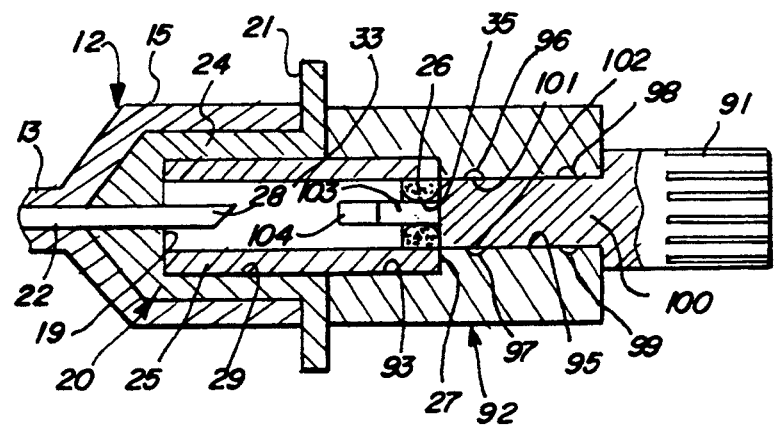
FIGS. 5A and 5B set forth partially sectioned side views of a still further alternate embodiment of the present invention integral catheter and blood tester in connected and disconnected orientation respectively.

FIG. 5A sets forth a still further alternate embodiment of the present invention catheter and blood tester generally referenced by numeral 80. Catheter and blood tester 80 utilizes catheter 12 and needle unit 20 together with sleeve 25 and valve 26 in the fabrication described above. Catheter and blood tester 80 differs from the preceding embodiments in the structure of tester housing 90 which utilizes a translating rod assembly to withdraw the contaminated test patch into the tester housing and thereby provide improved shielding of the blood contaminated test patch during handling by the practitioner.

Specifically, catheter 12 includes cylindrical housing 15 and intravenous tube 13 as described above. Similarly, needle unit 20 includes cylindrical housing 24, flange 21, closed end 19 and interior cavity 29, also described above. Cylindrical sleeve 25 is received within cavity 29 and defines an interior flash chamber 33 therein. Sleeve 25 extends outwardly beyond flange 21 terminating in an end 27. Valve 26 formed of a resilient material defines a constricting orifice 35 proximate end 27 of sleeve 25.

Tester housing 90 defines a generally cylindrical member formed of a clear transparent material such as clear molded plastic or the like and defines a cylindrical bore 95 together with a generally cylindrical cavity 94. The interior of cylindrical bore 95 defines a plurality of detent recesses 96 through 99 positioned along cylindrical bore 95 in accordance with the descriptions that follow. However, suffice it to note here that certain ones of recesses 96 through 99 are formed closer to cavity 94 while others are formed more remote therefrom.

A cylindrical rod 100 is sized to fit within cylindrical bore 95 in a sliding fit and defines a pair of outwardly extending projections 101 and 102. Projections 101 and 102 are configured to be receivable within detents 96 through 99. Rod 100 further includes an extended enlarged grip portion 91 at its outer end and an inwardly extending test strip 103 at the remaining end. Test strip 103 supports a test patch 104 which may, for example, comprise conventional litmus testing material or the like.

In the assembled position shown in FIG. 5A, tester housing 90 is received upon sleeve 25 and maintained in attachment to needle unit 20 by the frictional fit between inner diameter 93 of housing 90 and the outer surface of sleeve 25. Rod 100 is shown in FIG. 5A in its inserted testing position in which grip portion 91 abuts the outer edge of housing 90 and in which test strip 103 and test patch 104 extend through orifice 35 of valve 26 and into flash chamber 33. The position of rod 100 is maintained by the extension of projections 101 and 102 into detent recesses 96 and 97 respectively.

In operation, the above-described catheter insertion and blood flashing processes carried forward result in the introduction of a blood sample into flash chamber 33 which surrounds and wets test patch 104 producing the desired chemical reaction and visible changes of test patch 104. As mentioned above, this test may be a conventional reactive test in which the pH of the blood sample is tested using conventional litmus material for test patch 104. Alternatively, virtually any visual indicating test material may be utilized for test patch 104. Once the flashing process has confirmed the proper placement of the catheter needle, needle unit 20 and tester housing 90 may be withdrawn as a combined unit leaving catheter 12 in place for eventual coupling to a suitable intravenous unit in accordance with conventional practices.

Figure 5B:
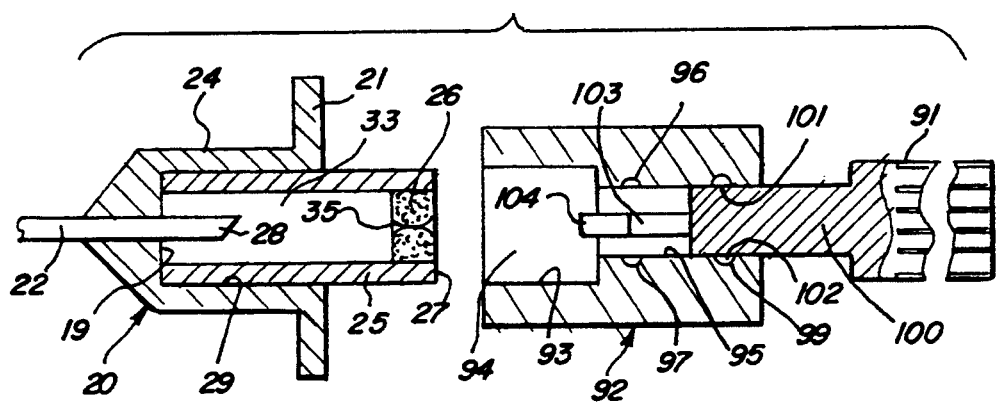

FIG. 5B sets forth the disassembled configuration of catheter and blood tester 80 following the separation of contaminated needle unit 20 from tester housing 90 which is carried forward in order to discard needle unit 20. The separation process is carried forward preferably by the practitioner gripping flange 21 and grip end 91 simultaneously and forcing needle unit 20 and tester housing 90 outwardly to simultaneously withdraw sleeve 25 from cavity 94 of tester housing 90. Concurrently, the separating force operates to draw rod 100 outwardly within cylindrical bore 95 and overcoming the detent action of projections 101 and 102 within recesses 96 and 97 respectively. Thus, rod 100 slides outwardly to the position shown in FIG. 5B until projections 101 and 102 are received within detent recesses 98 and 99 which maintains the relative position shown for tester housing 90 and rod 100. Once needle unit 20 is separated from tester housing 90, valve 26 closes orifice 35 captivating the blood sample within flash chamber 33. It should be noted that the constricting action of orifice 35 of valve 26 produces a wiping action upon test strip 103 and test patch 104 during the separation process which removes excess blood from test patch 104 permitting proper viewing of test patch 104 for the visual evaluation which follows. It should also be noted that the translating motion of rod 100 with respect to tester housing 90 causes blood contaminated test patch 104 and test strip 103 to be further withdrawn into the interior of tester housing 90 thereby further protecting the practitioner from inadvertent contamination and contact with potentially contaminated blood during the evaluation process. The clear transparent material of tester housing 90 permits the practitioner to easily view the condition of test patch 104 and thereby undertake the desired evaluation and comparison to standard color charts or the like. Once the evaluation has been completed, tester housing 90 may be discarded in accordance with standard precautionary techniques.

It should be noted that during the above-described handling of catheter and blood tester 80, the practitioner is protected from inadvertent contact with contaminated blood by the shielding action of the translating movement of rod 100 with respect to tester housing 90.

Figure 6A:
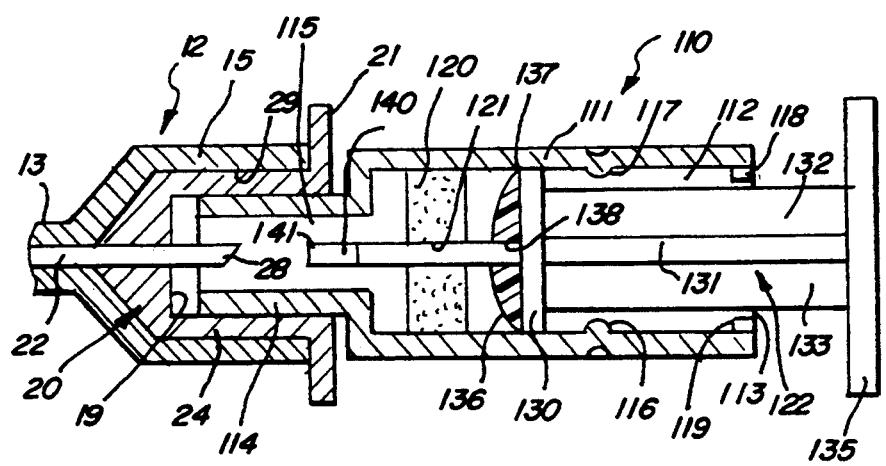
FIGS. 6A, 6B and 6C set forth partially sectioned side views of a still further alternate embodiment of the present invention integral catheter and blood tester in connected and disconnected orientation respectively.
Figure 6B:
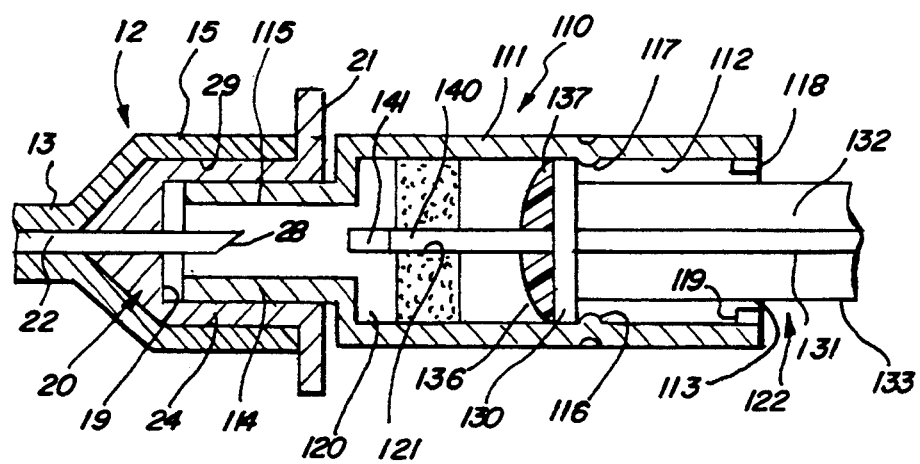
Figure 6C:
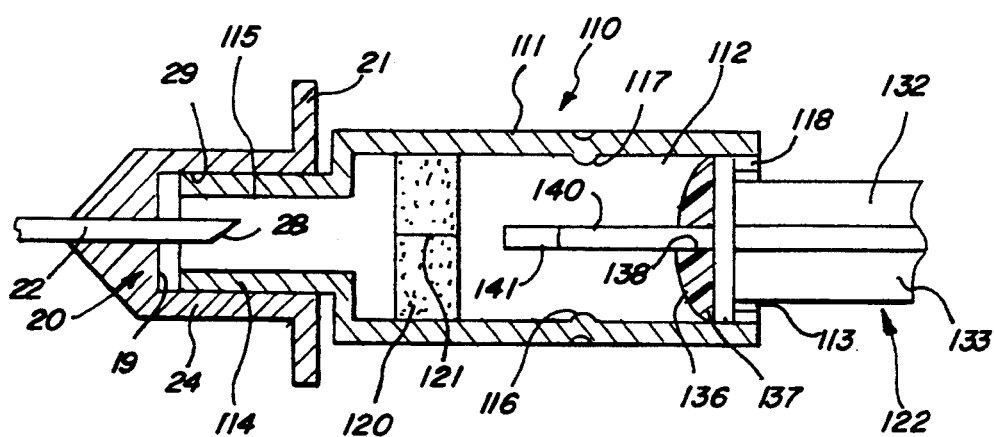

FIGS. 6A, 6B and 6C set forth the operation and structure of a still further alternate embodiment of the present invention blood tester. FIGS. 6A through 6C are shown in cross-section taken generally in the same manner set forth above in the above-described embodiments. FIG. 6A shows the initial position of the blood tester at the time of initial needle insertion. FIG. 61B sets forth the configuration of the blood tester following the above-described flashing operation which exposes the test patch to the patient's blood. FIG. 6C sets forth the final stage in the use of the embodiment of FIGS. 6A through 6C in which the test patch is withdrawn from the blood sample and is viewable while enclosed within the blood tester housing.

Specifically, FIG. 6A sets forth a section view of a blood tester constructed in accordance with the present invention and generally referenced by numeral 110. Tester 110 is used in combination with a catheter 12 constructed in accordance with conventional fabrication techniques and comprising a housing 15 having a hollow intravenous tube 13 extending therefrom. A catheter needle unit 20 includes a needle housing 24 supporting an elongated generally cylindrical needle 22 having a piercing end 23 (seen in FIG. 1) and an interior end 28. Needle housing 24 further defines an interior cavity 29 and a closed end 19 together with an extending flange 21. Needle unit 20 and catheter 12 are formed in accordance with conventional fabrication techniques.

Blood tester 110 includes a generally cylindrical housing 111 defining an interior cylindrical bore 112. Housing 111 terminates at one end in an open end 113 and at the remaining end in a reduced diameter portion 114. Reduced diameter portion 114 is generally cylindrical and configured to be received within cavity 29 of needle housing 24 in a tight generally sealing coupling. Reduced diameter end 114 defines an interior flash chamber 115.

A generally disk-shaped piston 130 is supported by an elongated generally cruciform-shaped rod 122. Rod 122 is formed of a quartet of mutually perpendicular webs 131, 132, 133 and a fourth web 134 (not seen). Rod 122 terminates at its outer end in a knob 135. In its preferred form, piston 130, rod 122 and knob 135 are integrally formed of a single molded plastic unit. An elongated preferably cylindrical test strip 140 is integrally formed with piston 130 and extends therefrom away from knob 135 toward flash chamber 115 of reduced diameter end portion 114. Test strip 140 supports a test patch 141 at the distal end thereof. An absorbent element 120 is interposed between piston 130 and flash chamber 115 and defines a center aperture 121. Absorbent element 120 is preferably formed of a somewhat resilient liquid absorbent material suitable for absorbing blood or other liquid materials. A piston seal 136 defines an aperture 138 and an outer sealing edge 137 which provides a tight sealing action against interior bore 112 of housing 111. A pair of inwardly extending detents 116 and 117 are formed in an intermediate position within cylindrical housing 111. In addition, a pair of inwardly extending stop tabs 118 and 119 are formed proximate open end 113 of housing 111.

In operation, tester 110 is coupled to needle unit 20 which in turn is received within catheter housing 115. The coupling of tester 110 to needle unit 20 is provided by the above-described tight fit insertion of reduced diameter end 114 into cavity 29. In the initial position shown in FIG. 6A, piston 130 is positioned in its forwardmost position of travel such that test strip 140 extends through aperture 121 of absorbent element 120 and thus test patch 141 extends into flash chamber 115. With the present invention tester thus positioned and assembled, the above-described process of catheter needle and intravenous tube 13 within the target blood vessel is undertaken. Once the target vessel has been pierced and needle 22 is in communication therewith, the above described flashing operation is carried forward.

FIG. 6B sets forth the next sequential position in the operation of tester 110 in which piston 130 and rod 122 have been withdrawn outwardly a short distance with respect to cylindrical housing 111 in the direction indicated by arrow 125. With piston 130 and piston rod 122 thus positioned, the outer surface of piston 130 contacts detents 116 and 117 to provide reliable positioning of test patch 141. As can be seen, test patch 141 remains in communication with flash chamber 115. During the outward movement of piston 130, a partial vacuum is produced within flash chamber 115 which aids the above-described flashing process and which assists the blood flow outwardly from end 28 of needle 22 into flash chamber 115 as shown by arrow 126. With the flashing operation initiated, the patient's blood sample within flash chamber 115 and the forwardmost portion of interior bore 112 communicates with test patch 141 causing test patch 141 to be appropriately exposed to the patient's blood sample and commencing the chemical reaction necessary for the visual indication. As described above, test patch 141 may utilize virtually any test material. For example, it has been found desirable to utilize a test patch material such as the commonly known litmus material to provide a pH sampling of the patient's blood.

At this point in the procedure, catheter 12 and needle 20 have been fully inserted into the patient's skin and target blood vessel. Thus, in accordance with user preference, needle unit 20 may be withdrawn from catheter housing 15 while still secured to tester 110 and thereafter discarded or, alternatively, tester unit 110 may be separated initially from needle unit 20 by withdrawing reduced diameter end portion 114 from cavity 29. In any event, once the blood sample within flash chamber 115 has sufficiently permeated test patch 141, piston 130 is further withdrawn in the direction of arrow 125 to the position shown in FIG. 6C.

FIG. 6C shows the final position of piston 130 within cylindrical housing 111. Once again, it should be noted that while FIG. 6C shows tester 110 having needle unit 20 remaining secured thereto, it may be desirable in accordance with preferred procedures to immediately withdraw tester unit 110 from needle unit 20 in order to properly dispose of needle unit 20. In either event, in the position shown in FIG. 6C, piston 130 has been withdrawn past detents 116 and 117 and has been withdrawn outwardly its maximum travel distance until piston 130 abuts stops 118 and 119. The outwardly movement of piston 130 draws test strip 140 and test patch 141 through aperture 121 of absorbent element 120. Absorbent element 120 provides a wiping action upon test patch 141 clearing the excess surface blood therefrom and exposing test patch 141 to visual observation.

Cylindrical housing 111 is fabricated of a clear transparent material such as molded plastic or the like and thus with tester 110 in the configuration shown in FIG. 6C, test patch 141 may be observed directly through cylindrical housing 111 while test patch 141 remains protectively enclosed within interior bore 112. As a result, the user is able to complete the pH testing of the blood sample by simple visual evaluation of the test patch using a material such as litmus or the like. If desirable for the user, piston 130 and stop limits 118 and 119 may be configured in accordance with conventional fabrication techniques to permit the complete withdrawal of piston 130, test strip 140, seal 136 and piston rod 122 from cylindrical housing 111. However, it has been found preferable to configure piston 130 to secure it within the interior of cylindrical housing 111 and thus provide positive and reliable protection for the user from exposure to the contaminated test patch.

What has been shown is a safe, convenient and easy to use integral catheter and blood tester which facilitates the implanting or inserting of a catheter needle together with preliminary blood testing such as pH testing or the like. The integral catheter and blood tester shown provides a sampling exposure of a test patch to the flashed blood within a flash chamber of the tester. Following flashing, the present invention integral catheter and blood tester is easily separated into a tester unit which may be maintained for visual testing and evaluation while separating off the contaminated and potentially dangerous catheter needle unit for discarding. The tester housing supports the exposed test patch within a clear transparent shielding structure which may be readily handled by the practitioner and which simultaneously protects the practitioner from inadvertent touching and contamination. The invention shown lends itself particularly advantageously to use during emergency or trauma site operations in which practitioners often must operate in the presence of high noise, confusion and excitement as well as the jostling ride in an ambulance or other emergency vehicle.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention.

That which is claimed is:

1. For use in testing a blood sample, an integral catheter and blood tester comprising:
    a catheter having a hollow tube;
    a needle unit having a needle unit housing partially removably received within said catheter, said needle unit housing defining an interior chamber and having a needle extending from said chamber terminating in a piercing end and removably received within said hollow tube;
    a blood tester having a blood tester housing removably couple to said needle unit, and said blood tester further comprising a test strip supported by said blood tester housing and supporting a test patch having a test surface, said test patch extending into said interior chamber when said blood tester housing is coupled to said needle unit;
    valve means supported by said needle unit for receiving said test strip and for wiping blood from said test surface when said blood tester housing and said needle unit are separated; and
    shield means, supported by said blood tester housing, for shielding and partially surrounding said test strip and test patch.

2. An integral catheter and blood tester as set forth in claim 1 wherein said needle unit includes an extending portion having a flash chamber therein communicating with said needle and supporting said valve means.

3. An integral catheter and blood tester as set forth in claim 2 wherein said blood tester housing includes an interior cavity for receiving said extending portion of said needle unit.

4. An integral catheter and blood tester as set forth in claim 3 wherein said test strip and test patch are supported within said interior cavity.

5. An integral catheter and blood tester as set forth in claim 4 wherein said valve means defining a resilient member having a closing orifice therein and wherein said test patch and test strip pass through said orifice when said needle unit and said blood tester housing are coupled.

6. An integral catheter and blood tester as set forth in claim 1 wherein said shield means include a transparent wall formed in said blood tester housing forming a transparent wall about said test patch and test strip.

7. An integral catheter and blood tester as set forth in claim 1 wherein said shield means include a transparent sleeve slidably supported upon said blood tester housing slidable between a retracted position and an extended position in which said sleeve extends beyond said test patch.

8. An integral catheter and blood tester as set forth in claim 7 wherein said shield means further includes spring means for urging said sleeve toward said extended position.

9. An integral catheter and blood tester as set forth in claim 1 wherein said blood tester housing defines a bore passage and wherein said blood tester includes a rod slidable within said bore passage, said rod having a first end extending into blood tester housing and supporting said test strip and said test patch and a second end extending outwardly from said housing terminating in a grip portion.

10. An integral catheter and blood tester as set forth in claim 9 wherein said rod is movable between a first position extending said test patch into said interior chamber and a second position in which said test patch is withdrawn into said blood tester housing.

11. For use by a user in testing a blood sample, a method of blood testing comprising the steps of:
    inserting a removable needle and an intravenous tube of a combination catheter and blood tester having an interior flash chamber and a test patch supported within said interior flash chamber into a blood vessel;
    flashing a quantity of blood into said flash chamber to wet said test patch;
    withdrawing said catheter needle and said blood tester from said intravenous tube;

separating said catheter needle from said blood tester and said test patch;

wiping excess blood from said wetted test patch during said separating step;

shielding said test patch from inadvertent contact with the user following separation; and visually observing said wiped test patch to evaluate said blood.

12. A blood tester for use in combination with a catheter, said blood tester comprising:

a blood tester housing defining an interior chamber and means formed in said blood tester housing for coupling said blood tester housing to the catheter;

a test strip having a test patch supported upon said test strip;

support means for supporting said test strip within said interior chamber and for exposing said test patch to said interior chamber and withdrawing it from said interior chamber; and wiping means for wiping said test patch when it is withdrawn from said interior chamber.

13. A blood tester as set forth in claim 12 wherein said blood tester housing defines a generally cylindrical passage and wherein said support means includes a piston movable within said generally cylindrical passage.

14. A blood tester as set forth in claim 13 wherein said piston includes an elongated rod extending toward said interior chamber and wherein said elongated rod supports said test strip so as to extend said test patch into said interior chamber when said piston is moved toward said interior chamber.

15. A blood tester as set forth in claim 14 wherein said piston defines a generally circular disk and wherein said test strip extends generally perpendicularly therefrom.

16. A blood tester as set forth in claim 15 wherein said support means includes a piston seal coupled to said piston.

17. A blood tester as set forth in claim 16 wherein said wiping means includes an absorbent member supported within said generally cylindrical passage interposed between said piston and said interior chamber and defining an aperture, said piston movable to extend said test strip through said aperture and to withdraw said test strip therefrom.

* * * * *